United States Patent [19]
Asoka kumar et al.

[11] Patent Number: 5,200,619
[45] Date of Patent: Apr. 6, 1993

[54] DETERMINATION OF INTERFACIAL STATES IN SOLID HETEROSTRUCTURES USING A VARIABLE-ENERGY POSITRON BEAM

[75] Inventors: Palakkal P. V. Asoka kumar, Coram; Kelvin G. Lynn, Center Moriches, both of N.Y.

[73] Assignee: Associated Universities, Inc., Washington, D.C.

[21] Appl. No.: 770,891

[22] Filed: Oct. 4, 1991

[51] Int. Cl.⁵ .............................................. H01J 37/00
[52] U.S. Cl. ..................................... 250/307; 250/308
[58] Field of Search ........................ 250/306, 307, 308

[56] References Cited

U.S. PATENT DOCUMENTS 4,864,131 9/1989 Rich et al. ............................ 250/306
5,015,851 5/1991 Singh et al. .......................... 250/307
5,063,293 11/1991 Rich et al. ........................... 250/307

OTHER PUBLICATIONS

*The Physics and Chemistry of $SiO_2$ and $SiO_2$ Interface*, Helms and Deal (eds), Plenum Press, New York (1988).
Schultz and Lynn, *Rev. Mod. Phys.*, 60, (1989).
Nielsen, Lynn et al., *Appl. Phys. Lett.*, 51, 1022 (1987).
Nielsen, Lynn et al., *Phys. Rev.*, B40, 1434 (1989).
Lynn, Nielsen et al., *Can. J. Phys.*, 67, (1989).
Uedono et al., *Phys. Lett.*, 133A, 83 (1988).
Zhang et al., *Appl. Surf. Sci.*, 39, 374 (1989).
Lynn et al., *Appl. Phys. Letter.*, 47(b) 239 (1985).
Canter, "Positron Studies of Solids, Surfaces and Atoms", 103, World Scientific, N.Y., N.Y. (1986).
Nicollin et al., "MOS (Metal Oxide Semiconductor)", *Physics and Technology*, p. 789, John Wiley & Sons, New York, (1982).
Asoka-Kumar, Lynn et al., *J. Appl. Phys.*, 69, 6603–6606 (May 1991).
Yeow et al., *J. Phys. D: L Appl. Phys.*, 8, 1495 (1975).
*Positrons in Solids*, Hautojarvi (Ed.), Springer-Verlag, New York (1979).
Asoka-Kumar & Lynn, "Implantation Profile of Low-energy Positrons in Solids", *Appl. Phys. Lett.* 57, 1634–1636 (Oct. 15, 1990).
Mantl and Triftshauser, *Phys. Rev. B*, 17, 1645 (1978).
Fare et al., *J. Appl. Phys.*, 63, 5507 (1988).
Lynn & Asoka-Kumar, "Proceedings of the 2nd Workshop on Researchers Using Positrons, Feb. 28–Mar. 1, 1991", *Japan Atomic Energy Research Institute, Takasaki Radiation Chemistry Research Establishment*, 9-2 132–141 (1991).
Schultz et al., *Phys. Rev. Lett.*, 61(2), 187–190 (1988).

*Primary Examiner*—Bruce C. Anderson
*Attorney, Agent, or Firm*—Margaret C. Bogosian

[57] ABSTRACT

A method and means is provided for characterizing interfacial electron states in solid heterostructures using a variable energy positron beam to probe the solid heterostructure. The method includes the steps of directing a positron beam having a selected energy level at a point on the solid heterostructure so that the positron beam penetrates into the solid heterostructure and causes positrons to collide with the electrons at an interface of the solid heterostructure. The number and energy of gamma rays emitted from the solid heterostructure as a result of the annihilation of positrons with electrons at the interface are detected. The data is quantified as a function of the Doppler broadening of the photopeak about the 511 keV line created by the annihilation of the positrons and electrons at the interface, preferably, as an S-parameter function; and a normalized S-parameter function of the data is obtained. The function of data obtained is compared with a corresponding function of the Doppler broadening of the annihilation photopeak about 511 keV for a positron beam having a second energy level directed at the same material making up a portion of the solid heterostructure. The comparison of these functions facilitates characterization of the interfacial states of electrons in the solid heterostructure at points corresponding to the penetration of positrons having the particular energy levels into the interface of the solid heterostructure. Accordingly, the invention provides a variable-energy non-destructive probe of solid heterostructures, such as $SiO_2$/Si, MOS or other semiconductor devices.

12 Claims, 9 Drawing Sheets

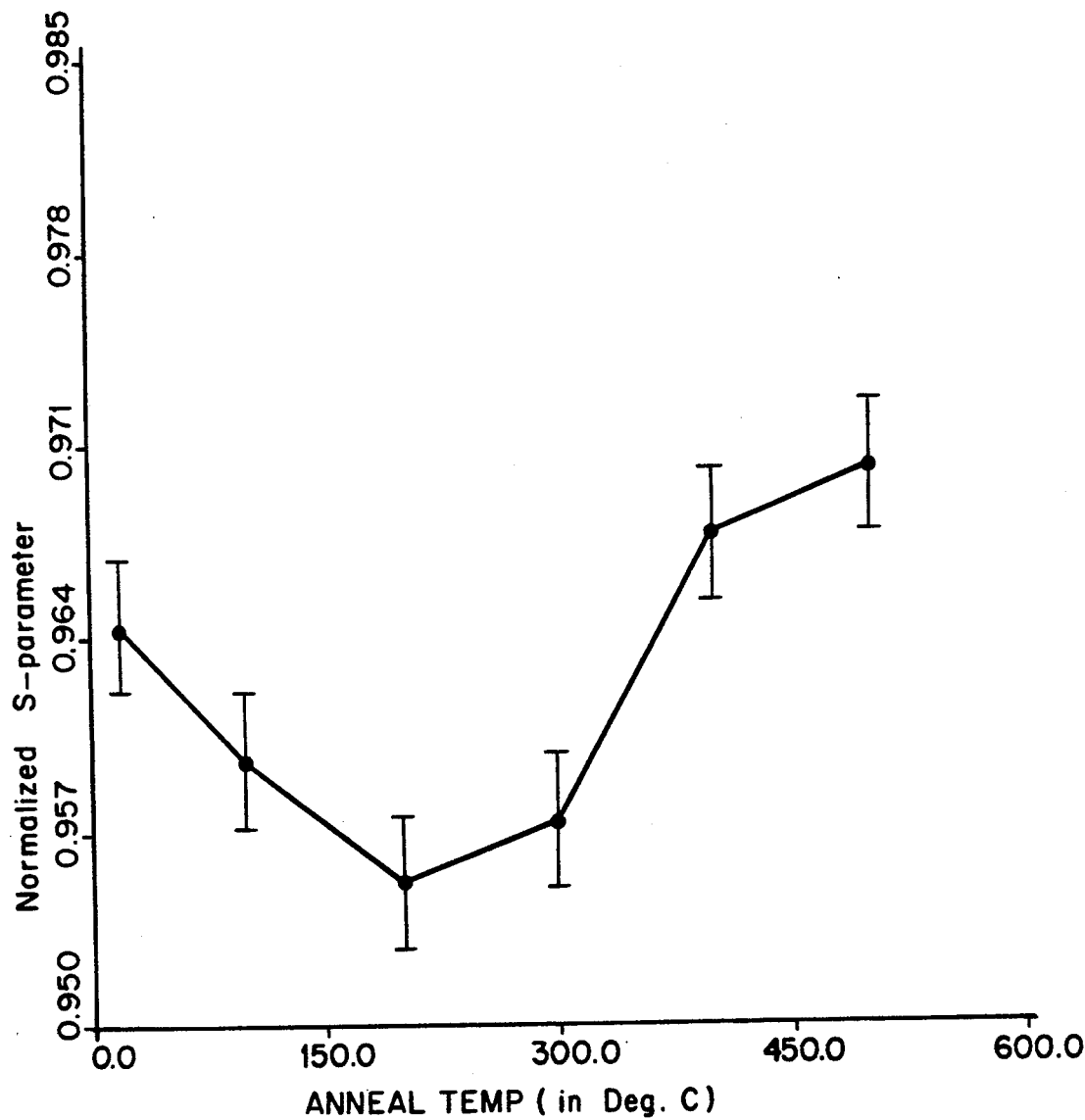

DETERMINATION OF INTERFACIAL STATES IN SOLID HETEROSTRUCTURES USING A VARIABLE-ENERGY POSITRON BEAM

BACKGROUND OF THE INVENTION

The invention was supported by the U.S. Department of Energy under contract No. DE-AC02-76CH00016. Accordingly, the United States Government has certain rights in this invention.

FILED OF THE INVENTION

This invention relates to a method and means for characterizing and measuring the interfacial states in solid heterostructures, such as MOS or other semiconductor devices using a variable-energy positron beam to provide a non-destructive probe of the solid heterostructures.

BACKGROUND OF THE RELATED ART

Silicon has been in a unique position in the semiconductor industry due largely to the ease of making a passive, water-insoluble masking film and growing or depositing an oxide film on its surface. The nature of the interface region in the Si/SiO$_2$ systems show large variation depending on the processing techniques; see for Example: *The Physics and Chemistry of SiO$_2$ and SiO$_2$ Interface.* Helms and Deal (eds), Plenum Press, New York (1988). Adverse interface properties, such as a large number of charge trap centers, can alter or hinder the electrical behavior of the oxide-semiconductor structure. Commercial interest in detecting and eliminating these irregularities stimulated intense research efforts to understand and improve the quality of the interface properties. In particular it has been observed that the density of the interface traps can be altered by orders of magnitude by a low-temperature annealing of the sample in different ambient gases. Even though the process by which the trap centers are activated or passivated are not well understood, it is definitely affected by hydrogen, thought to be atomic in nature.

Positron annihilation studies of solid materials have grown rapidly in recent years because of the advances in the development of relatively intense, low-energy positron beams, as reviewed by Schultz and Lynn, *Rev Mod. Phys.*, 60, 701 (1988). These studies utilize the fact that the positron annihilation process is entirely decided by the initial state of the positron-many electron system. When positrons are implanted in a solid they are rapidly thermalized ($\sim$1-10 ps), and these positrons annihilate with electrons either directly or after forming a bound system known as positronium. In the case of direct annihilation two 511 keV $\gamma$-rays are produced, which are broadened by the motion of the electrons and positrons prior to the annihilation. Since the thermalized positrons have much lower momentum compared to electrons in the solid, the Doppler broadening of the 511 keV $\gamma$-spectrum will depend mostly on the electron motion. Hence the annihilation spectra have been used to extract information about the electron environment around the annihilation site. As positrons are increasingly employed as a probe to study surface properties, interface structures and defect profiles, a proper prescription of the implantation profile and means for data analysis is needed.

Variable energy positron beams have recently been applied to the study of SiO$_2$/Si structures and has shown new results because of the unique depth and defects information they can provide. See, for Example, Nielsen, Lynn et al., *Appl. Phys. Lett.*, 51, 1022 (1987); Nielsen, Lynn et al. *Phys. Rev.*, B40, 1434 (1989); Lynn, Nielsen et al., *Can. J. Phys.*, 67, (1989) and Uedono et al., *Phys. Lett.* 133A, 83 (1988). Existing variable-energy positron beam experiments have exclusively been measuring the Doppler broadening by characterizing the annihilation lineshape with a lineshape parameter known as S-parameter; see Schultz and Lynn (1988), supra. The S-parameter technique has been applied in several detailed studies like SiO$_2$/Si interface, see Nielsen, Lynn et al. (1987) supra., and Nielsen, Lynn et al. (1989) supra.; to the hydrogen-sensitive interfacial defects, see Lynn, Nielsen et al. (1989) Supra.; and to electric field effect at the Si surface, Uedono, Tanagawa et al. (1988) supra.

For many years various experimental techniques have been used to identify and understand the properties of the interface and its trapping centers, for Example capacitance-voltage measurements (CV), electron spin resonance (ESR), transmission electron microscopy (TEM), etc. Most of these techniques, however, are either destructive or requires special preparation. In some cases the measurement process itself permanently alters the electrical properties of the SiO$_2$/Si wafer. Therefore, it would be desirable to devise a non-destructive and depth resolving technique, which could probe semiconductor devices, such as MOS, for quality control, research and testing in the semiconductor industry.

SUMMARY OF THE INVENTION

These and other purposes are achieved by the present invention which provides a process utilizing means for characterizing and measuring interfacial states in solid heterostructures, such as SiO$_2$/Si, MOS and other semiconductor devices using a variable-energy positron beam. The present invention provides a non-destructive probe of the solid heterostructures. The method of the present invention is accomplished by directing a positron beam having a first energy level at a first point of solid heterostructure. The first energy level is sufficient for the positron beam to penetrate into the solid heterostructure and collide with electrons a: an interface of the solid heterostructure. The number and energy of gamma rays emitted from the solid heterostructure as a result of positrons annihilating with electrons at the interface of the solid heterostructure are detected. The data obtained is quantified as a function of the Doppler broadening of a photopeak about the 511 keV line created by the annihilation of the positrons and electrons at the interface of the solid heterostructure; preferably as a S-parameter or W-parameter function, and further quantified as a normalized S-parameter or W-parameter function, respectively.

The corresponding function may be obtained either by directing the positron beam at another point of the solid heterostructure at the same or different energy level; or at the same point of the solid heterostructure depending on the particular aspect of the solid heterostructure being analyzed. Likewise the second positron beam may have the same, a lower or a greater energy level as the first positron beam. In addition, physical or chemical conditions, such as annealling temperature or chemical impurities at the interface, in the manufacture or treatment of the solid heterostructure may be varied or introduced prior to directing the second positron beam at the solid heterostructure. A comparison of these functions facilitates a characterization of the interfacial state of electrons in the solid heterostructure at points which correspond to the penetration of the positron beam into the interface of the solid heterostructure.

For a better understanding of the present invention, reference is made to the following description and Examples taken in conjunction with accompanying equations and figures, the scope of which is pointed out in the appended claims.

BRIEF DESCRIPTION OF THE DRAWINGS

FIGS. 3A, 3B, and 3C graphically show the normalized S-parameter of values as a function of annealing temperature for different incident positron energies of 3.47 keV, 4.47 keV and 5.47 keV, respectively. Each of these experiments were carried out on a Si/SiO$_2$ target having a 108.1 nm thickness manufactured in a dry, no HCl environment with the measurements taken at room temperature.

DETAILED DESCRIPTION OF THE INVENTION

Figure 1:
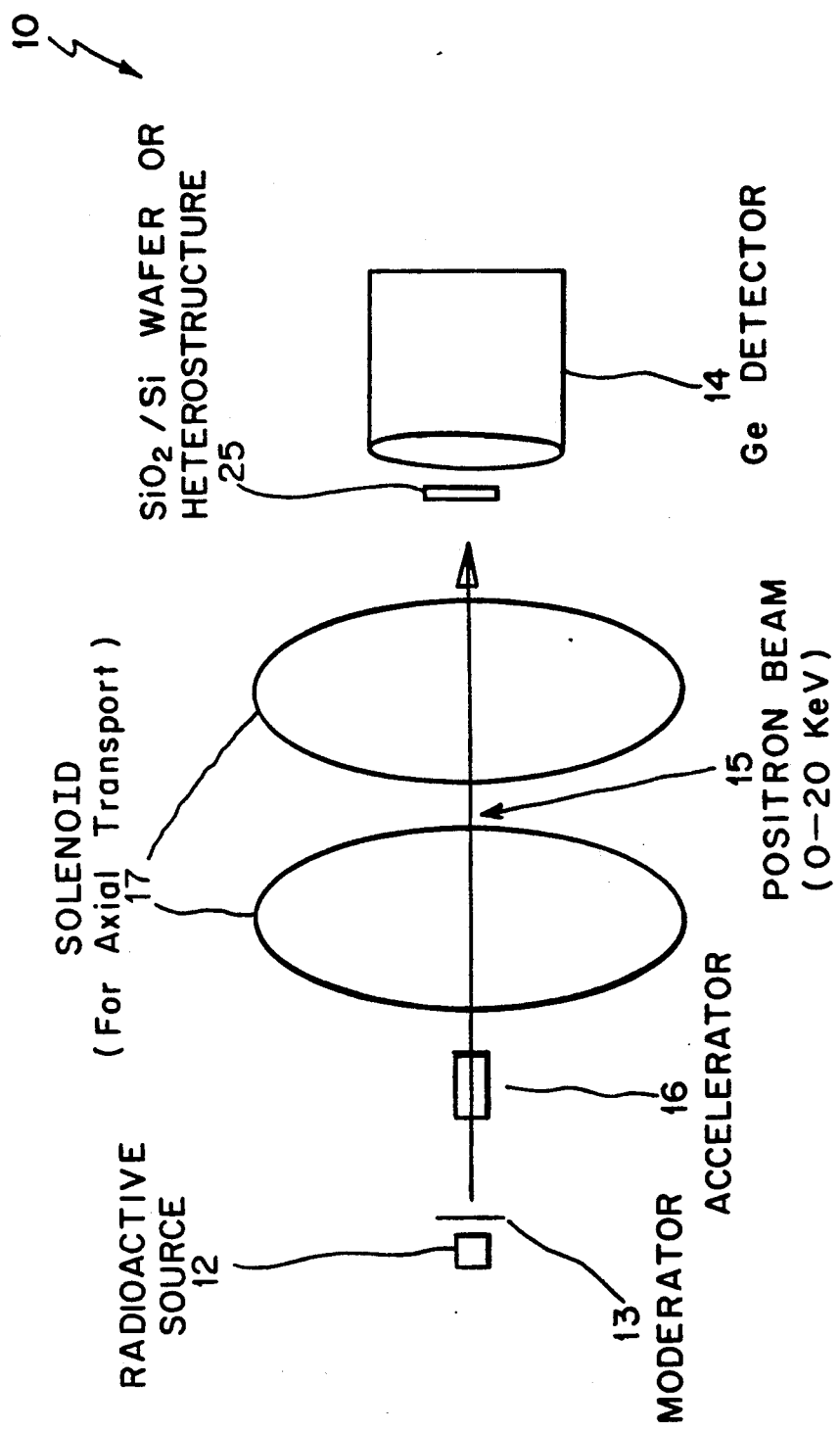
FIG. 1 is a schematic diagram of one preferred apparatus for carrying out the method of the present invention.

The present invention provides a process and means for characterizing and measuring interfacial states in solid heterostructures, such as SiO$_2$, MOS and other semiconductor devices using a variable-energy positron beam. The present invention provides a non-destructive probe of the solid heterostructures. The apparatus 10 was used in the foregoing Examples for carrying out the method of the present invention is shown in FIG. 1. It produces an intense, variable-energy positron beam 15 by moderating positrons from a β+ decaying radioactive source 12 (Na$^{22}$) with the aid of a single crystal moderator 13, suitably made of tungston of high efficiency, typically $5 \times 10^{-4}$ fast positrons are moderated, and a high resolution germanium detector 14 with associated read out devices. The moderated positron beam is accelerated to the desired energy with a linear accelerator 16 and is transported to a target 25 by means of an axial magnetic field produced by a series of solenoids 17. The specifics of constructing positron beam generators suitable for the present invention are well known in the art, for example as described in detail by Lynn et al., Appl. Phys. Lett., 47(b), 239 (1985).

Figure 2:
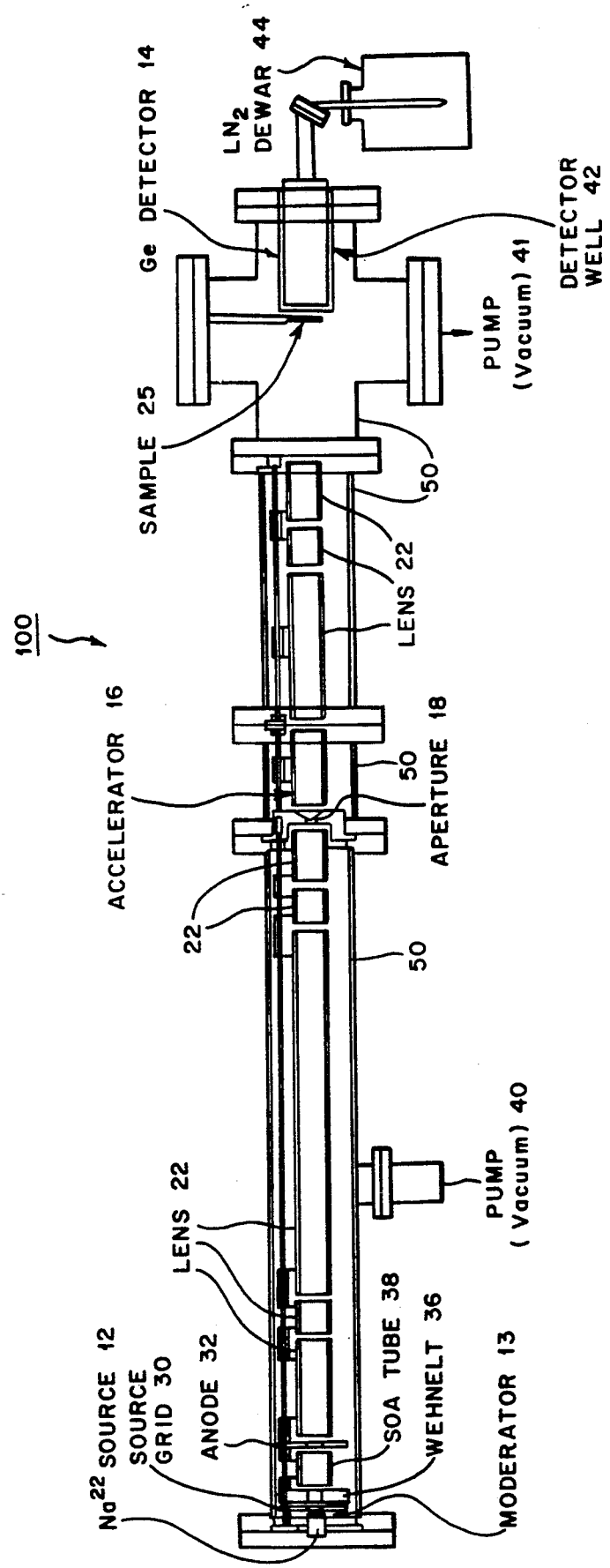
FIG. 2 is a detailed schematic of another apparatus which can suitably be employed for interface characterization in accordance with the present invention.

A detailed schematic of another suitable apparatus which can be employed for interface characterization in accordance with the present invention is illustrated in FIG. 2. As shown in FIG. 2, positrons generated from a $^{22}$Na source 12 pass through a source grid 30 and are moderated with the aid of a single crystal moderator 13, suitably made from tungsten for these experiments, so as to produce monoenergetic positrons. The moderated positrons are extracted with the aid of Wehnalt 36, Soa tube 38 and anode 32, as described by Canter, "Positron Studies of Solids, Surfaces and Atoms", 103, World Scientific, N.Y., N.Y. (1986). The extracted positron beam is focused and transported through a small aperture 18 (~4 mm in diameter) located 75 cm from the source by a set of lens elements 22. The focused positron beam is accelerated to the desired energy by means of accelerator 16, transported and focused by lens elements 22 onto the sample 25, which is situated in front of Ge detector 14 cooled by LN$_2$ dewar 44. The final beam diameter is estimated to be less than 2 mm. The positron beam energy can be varied from 0.05 to 100.0 keV. The positron beam intensity during these experiments was $5 \times 10^5$ e+/s and was too low to produce any measurable radiation damage in the sample. The annihilation γ-rays were recorded in a Ge detector 14 of high efficiency and high resolution (0.24% and 1.4 keV-full width at half maximum, respectively) with associated readout and storage devices.

Specifically, the signal from the Ge detector 16 is amplified (using model #444 & 673, EG&G Ortec, 100 Middland Road, Oak Ridge, Tenn. 37831), and digitized with an analog to digital converter (Model #8077, Canberra Industries, Inc., One State Street Meridian, Conn. 06450). The digital signal is sent to a multi-channel analyzer (Model #S100, Canberra Industries, Inc.) residing in a computer (system 325, Dell Marketing Corporation, Public Sector, P.O. Box 9986, Austin, Tex. 78759) for storage and analysis.

In carrying out the Examples a 1081 Å thick, thermally grown (dry/no HCL) SiO$_2$/Si (100 orientation) wafers 25 were utilized. Each wafer has an n-type substrate of resistivity 16 ohm-cm and a doping density of $10^{16}$/cm$^3$ phosphorus. The wafers were not subjected to a post-oxidation anneal. Each sample 25 was annealed in situ during the Examples by a resistively heated tantalum foil, which also acted as part of the mounting assembly for the sample. The temperature of the sample 25 was continuously monitored by a computer with a readout from a thermocouple that was in contact with the sample. A suitable thermocouple, which was used for these experiments is the K-type Chromel-Alumel thermocouple, manufactured by Omega Engineering Inc., One Omega Drive, Stanford, Conn., 06907. The thermocouple was calibrated prior to the experiment with a single color infrared pyrometer. A suitable pyrometer, which was used for these experiments is the Pulsar 11 model No. 7000GP, manufactured by E$^2$T Technology Corp., Ventura, Calif., 93003.

The entire apparatus (either 10, or 100) is housed in airtight Chambers) 50 which are evacuated by pump(s) 40, 41. The actual temperature of the samples was estimated to be within ±20° C. of the measured value. The base pressure in the target chamber ranged from a low of about $(1 \times 10^{-8})$ to a high of about $(7 \times 10^{-8}$ torr. The annihilation spectra was recorded in the Ge detector 14 located behind the sample 25 as shown in FIGS. 1 and 2. All measurements refer to 1 million events recorded in the Ge detector 14, The inventors herein recognize, however, that this apparatus can be modified by those of ordinary skill in the art, depending on the particular design requirements of an on-line processing facility for semiconductor wafer production or for other applications.

In using this apparatus 10 the method of the present invention includes the steps of directing a positron beam having a first energy level at a first point of solid heterostructure. The first energy level is sufficient for the positron beam to penetrate into the solid heterostructure and collide with electrons at an interface of the solid heterostructure. The intensity and energy of gamma rays emitted from the solid heterostructure as a result of positrons annihilating with electrons at the interface of the solid heterostructure are detected. The data obtained is quantified as a function of the Doppler broadening of a photopeak about the 511 keV line created by the annihilation of the positrons and electrons at the interface of the solid heterostructure; preferably as a S-parameter or W-parameter function, and further quantified as a normalized S-parameter or W-parameter function, respectively.

The corresponding function may be obtained as described above, and discussed in more detail by Schaltz and Lynn (1988) supra., either by directing the positron beam at another point of the solid heterostructure at the same or different energy level; or at the same point of the solid heterostructure depending on the particular aspect of the solid heterostructure being analyzed. Likewise the second positron beam may have the same, a lower or a greater energy level as the first positron beam. In addition, a physical condition in the manufacture or treatment of the solid heterostructure may be varied prior to directing the second positron beam at the solid heterostructure. A comparison of these functions facilitates a characterization of the interfacial state of electrons in the solid heterostructure at points which correspond to the penetration of the positron beam into the interface of the solid heterostructure.

Figure 5A:
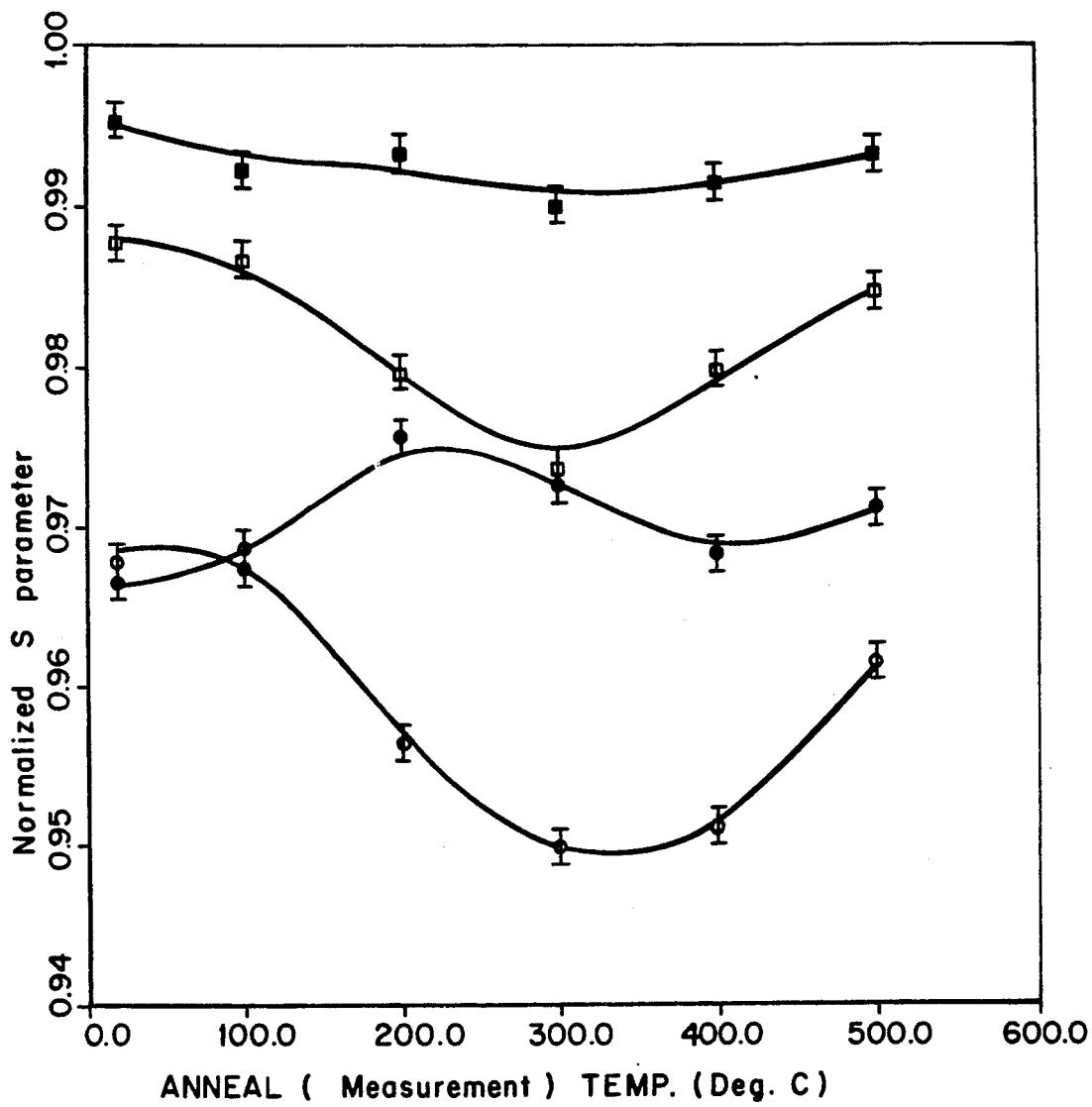
FIGS. 5A and 5B show the normalized S-parameter curves as a function of annealing temperature for four (4) mean implantation depths, 240 Å (●), 1130 Å (o), 2775 Å , and 4786 Å (□). The measurements shown in FIG. 5A were performed at the annealing temperature, and the measurements shown in FIG. 5B were performed at room temperature after each annealing cycle. The 1130 Å curves probe the interface region and show a reduction for 200°–400° C. the lines through the data points are drawn as a guide to the eye.
Figure 5B:
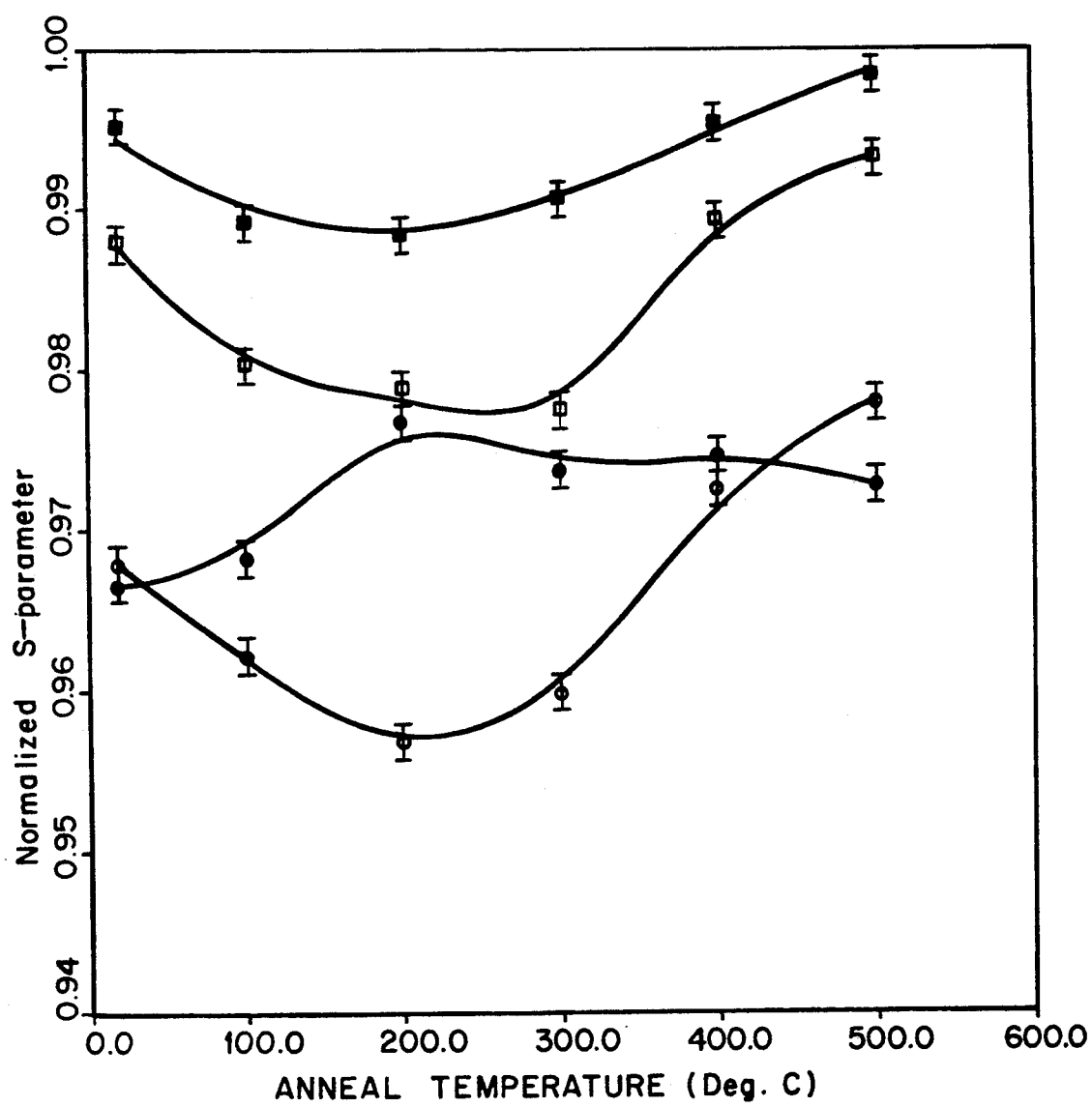

When a positron annihilates with an electron, γ-rays are created at an energy of 511 keV. If the electron or positron are in motion before the annihilation, the 511 keV γ-line will be broadened and the broadening will be decided by the initial momentum of the annihilating pair, which is defined as Doppler broadening. One way the Doppler broadening of the annihilation photopeak can be quantified is by introducing a simple line-shape parameter. The most commonly used line-shape parameter is known as S (for shape) parameter. The S-parameter is defined as the ratio of the number of counts in a small central region around the 511 keV line to the total number of counts in the photopeak; for Example as shown in FIGS. 5A or 5B. Since the Doppler broadening is predominantly influenced by the electron momentum, a higher S-value will be associated with an annihilation site where positrons are more likely to encounter electrons of lower momentum. The width of the central portion can be arbitrarily defined as long as the definition is not changed during one set of measurements.

Alternately, a W-parameter, called the wing parameter, is defined as the ratio of the counts in the wing of the photopeak of the total counts in the photopeak; again see FIGS. 5A or 5B. Either the S-parameter or the W-parameter can be used to extract the information about the environment in which the positron annihilates. Even though the Examples provide data and analysis of changes in the S-parameter plots, it should be noted that a W-parameter plot or any other parameter that can be used to characterize the Doppler broadening of the photopeak can also be used to show the interface signal. Additionally, a life-time measurement of positrons implanted at the interface can produce an analogous result.

A normalized S-parameter is defined as the ratio of the S-parameter for a given energy value to the S-parameter corresponding to bulk silicon. The normalized S-parameter is used to reduce any systematic errors between different sets of measurements. The bulk S-parameter (denoted by $S_b$) is extracted by a non-linear fitting procedure as described below. The bulk S-parameter can also be evaluated by averaging the S-parameter values for higher incident positron energies, i.e. in Example 2, 15.0 to 20.0 keV, and are in agreement with the fitted values.

In the Examples, the positron beam energy is step-wise increased from 0.0 to 20.0 keV. For each energy value, the S-parameter is evaluated with 1 million events recorded by a Ge detector. As the positron energy is increased, the positrons penetrate deeper into the sample. At first the S-parameter corresponds to the SiO$_2$ overlayer, then the interface, and finally the bulk Si. An annealing series performed in the Examples on the SiO$_2$/Si sample changes the interface S-parameter signal, which is shown on normalized S-parameter plot. One of the most important observations in such measurements is that one can rapidly extract the changes occurring at the interface, depending on the intensity of the positron beam utilized, by measuring the changes in the S-parameter corresponding to the interface.

Figure 4:
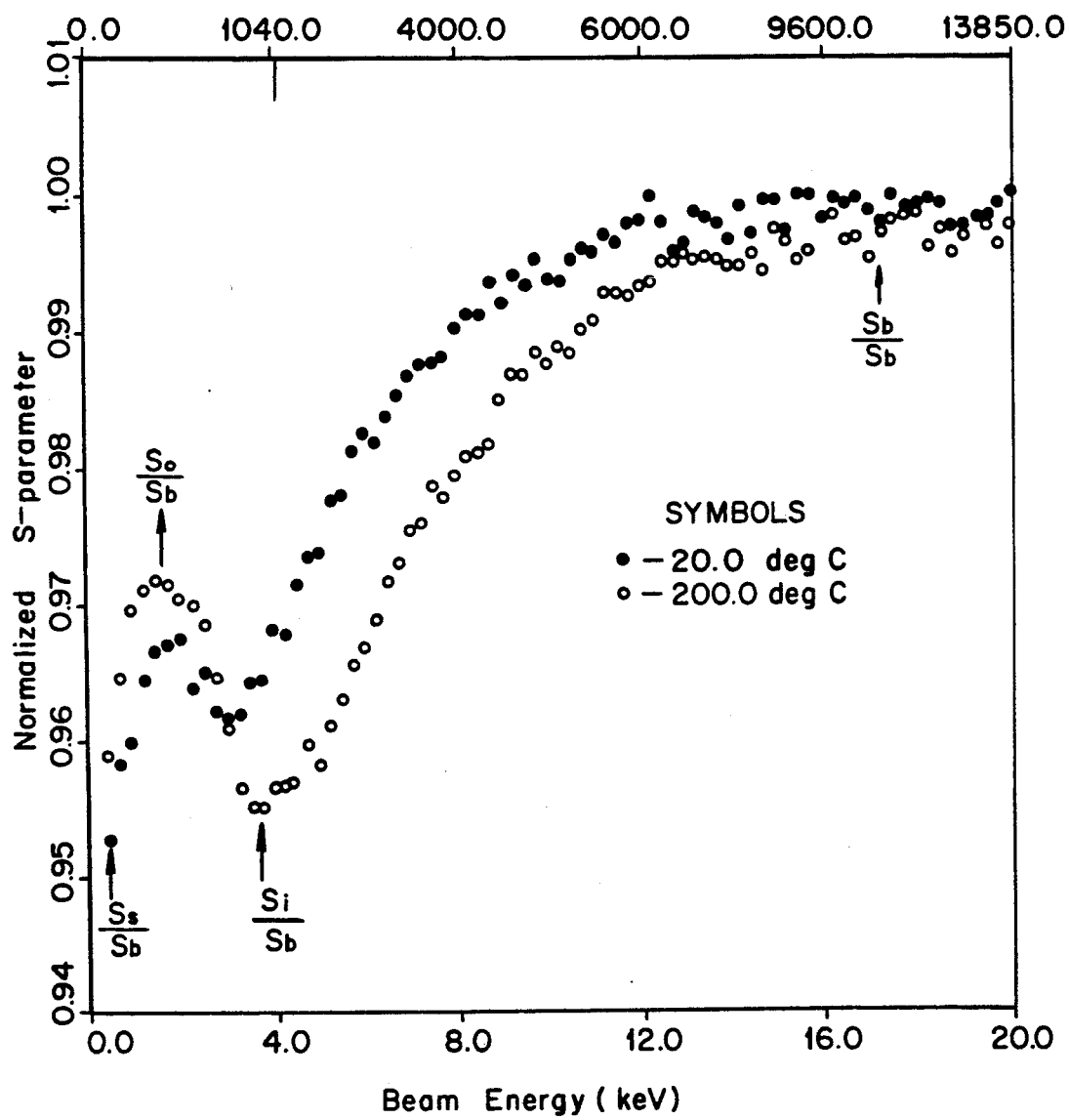
FIG. 4 is a graph showing the normalized S-parameter data as a function of the estimated mean implantation depth, i.e. incident positron energy, for measurements performed at room temperature before ● and after (o) annealing at 200° C. The tick mark at 1081 Å on the horizontal axis indicates the interface location. The first data points on the left of each set are associated with the surface parameter $S_s$. The initial rise corresponds to the overlayer $S_o$ and the immediate lowering to the interface $S_i$. The curve saturates at a bulk value $S_b$ for large implantation depth, i.e. large implantation energy.

Typical normalized S-parameter curves (i.e. divided by $S_b$) measured at room temperature are shown in FIG. 4. Four distinct signals corresponding to the surface, overlayer, interface, and the bulk silicon represented by $S_s/S_b$, $S_o/S_b$, $S_i/S_b$, and $S_b/S_b$, respectively, are clearly evident. To compare changes associated with annealing at different regions of the SiO$_2$/Si system, normalized S-parameter versus annealing temperature are plotted in FIG. 5A, corresponding to mean penetration depths of 240, 1130, 2775, and 4785 Å, respectively.

In FIGS. 5A and 5B the normalized S-parameter for the overlayer, represented by 240 Å data points, show only small changes under heating. However, as the beam energy was increased to the point that more positrons are stopped near the interface region, a reduction in the normalized S-parameter was observed corresponding to annealing temperatures from 200° to 400° C. The normalized S-parameter corresponding to the interface region is reduced by about 0.0180.

Figure 6:
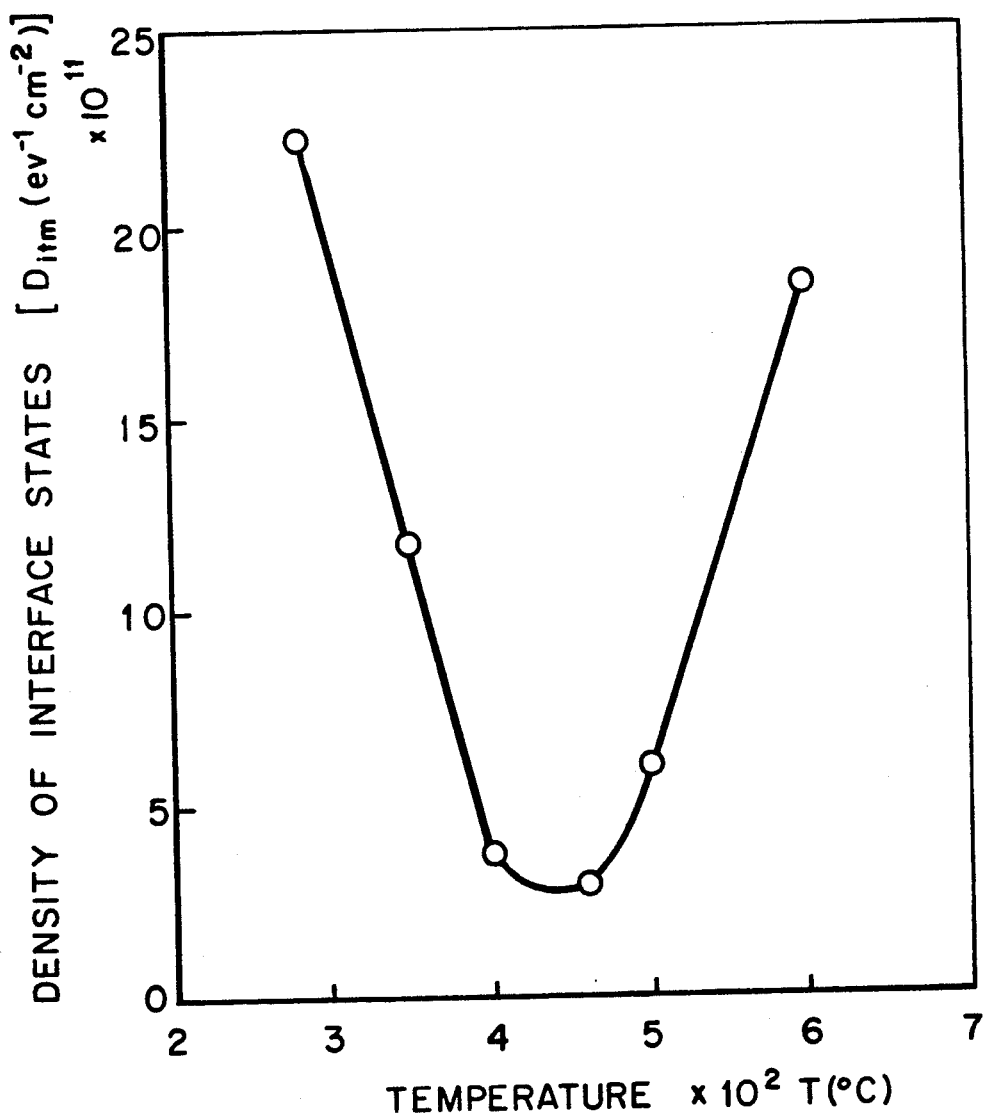
FIG. 6 is a graph showing the density of interface states versus temperature using a standard CV techniques on an SiO$_2$/Si system at temperatures from 200°–600° C. This figure is taken from Zhang et al., Appl. Surf. Sci., 39, 374 (1989) and shows that annealing at 200°–400° C. reduced the interface state density in a strikingly similar fashion as shown in FIGS. 2–5, above.

Accordingly, in performing the annealing series on the sample the following Examples demonstrate that the method of the present invention is sensitive to interface changes. The observed changes in the normalized S-parameter as a function of the annealing temperature of FIG. 5 can be understood in terms of the changes occurring in the interface state densities as shown in FIG. 6.

EXAMPLES

1. Experimental Apparatus

The apparatus 10 employed in the present invention is shown in FIG. 1. It produces an intense, variable-energy positron beam 15 by moderating positrons from a $\beta+$ decaying radioactive source 12 ($Na^{22}$) with the aid of a single crystal moderator 13 (made from tungston) of high efficiency, typically $5 \times 10^{-4}$ fast positrons are modulated, and a high resolution germanium detector 14 with associated read out devices. The moderated positron beam is accelerated to the desired energy by a linear accelerator 16 and is transported to a target 25 by means of an axial magnetic field produced by a series of solenoids 17, A schematic representation of the apparatus 10 used in these experiments is shown in FIG. 1. The specifics of constructing positron beam generators suitable for the present invention are described in detail by Lynn et al., *Appl. Phys. Lett.*, 47(b), 239 (1985).

As illustrated in FIG. 1, positrons generated from a $^{22}$Na source 12 are moderated with a single crystal moderator 13, suitably made from tungsten for these experiments, so as to produce monoenergetic positrons. The moderated positrons are extracted (not shown), accelerated through accelerator 16, and transported by solenoids 17 onto the sample 25, which is situated in front of Ge detector 14. The final beam diameter Was estimated to be less than 6 mm. The positron beam energy can be varied from 0.05 to 100.0 keV. The positron beam intensity during these experiments was $5 \times 10^5$ e+/s and was too low to produce any measurable radiation damage in the sample. The annihilation $\gamma$-rays were recorded in a Ge detector 14 of high efficiency and high resolution (0.24% and 1.4 keV-full width at half maximum, respectively) with associated readout and storage devices.

Specifically, the signal from the Ge detector 16 was amplified (using model #444 & 673, EG&G Orte, 100 Middland Road, Oak Ridge, Tenn. 37831), and digitized with an analog to digital converter (Model #8077, Canberra Industries, Inc., One State Street Meridian, Conn. 06450). The digital signal is sent to a multi-channel analyzer (Model #S100, Canberra Industries, Inc.) residing in a computer (system 325, Dell Marketing Corporation, Public Sector, P.O. Box 9986, Austin, Tex. 78759) for storage and analysis.

These Examples utilized 1081 Å thick, thermally grown (dry/no HCL) $SiO_2/Si$ (100 orientation) wafers 25. Each wafer has an n-type substrate of resistivity 16 ohm-cm and a doping density of $10^{16}/cm^3$ phosphorus. The wafers were not subjected to a post-oxidation anneal. Each sample 25 was annealed in situ during the Examples by a resistively heated tantalum foil, which also acted as part of the mounting assembly for the sample.

The temperature of the sample 25 was continuously monitored by a computer with a readout from a thermocouple that was in contact with the sample. A suitable thermocouple, which was used for these experiments is the K-type Chromel-Alumel thermocouple, manufactured by Omega Engineering Inc., One Omega Drive, Stanford, Conn., 06907. The thermocouple was calibrated prior to the experiment with a single color infrared pyrometer. A suitable pyrometer, which was used for these experiments is the Pulsar 11 model No. 7000GP, manufactured by $E^{22}T$ Technology Corp., Ventura, Calif., 93003.

The actual temperature of the samples was estimated to be within $\pm 20°$ C. of the measured value. The base pressure in the target chamber ranged from low of about $(1 \times 10^{-8}$ a torr) to a high of about $(7 \times 10^{-8}$ torr). The annihilation spectra was recorded in the Ge detector 14 located behind the sample 25 as shown in FIG. 1. All measurements refer to 1 million events recorded in the Ge detector 14.

EXAMPLE 1

In this Example the positron beam energy was stepwise increased to 3.47 keV, 4.47 keV and 5.57 keV to probe different depths of $SiO_2/Si$ wafer samples 25. The annihilation rate recorded by the detector 14 remained essentially the same throughout the course of the experiment.

The positrons impinging on the sample 25 thermalized rapidly and the positrons produced annihilation $\gamma$-rays when they annihilated with electrons. Since the momentum of the thermalized positron is usually much smaller than the momentum of the electron participating in the annihilation, the width of the resulting $\gamma$-ray spectrum is dominated by the momentum of the electron. Hence the annihilation spectrum of positrons carries the signature of the local environment of the annihilation site through the Doppler broadening of the annihilation photopeak. An S-parameter, defined as the ratio of the counts in a central region of the annihilation photopeak to the total counts in the photopeak was used to quantify this information.

Figure 3B:
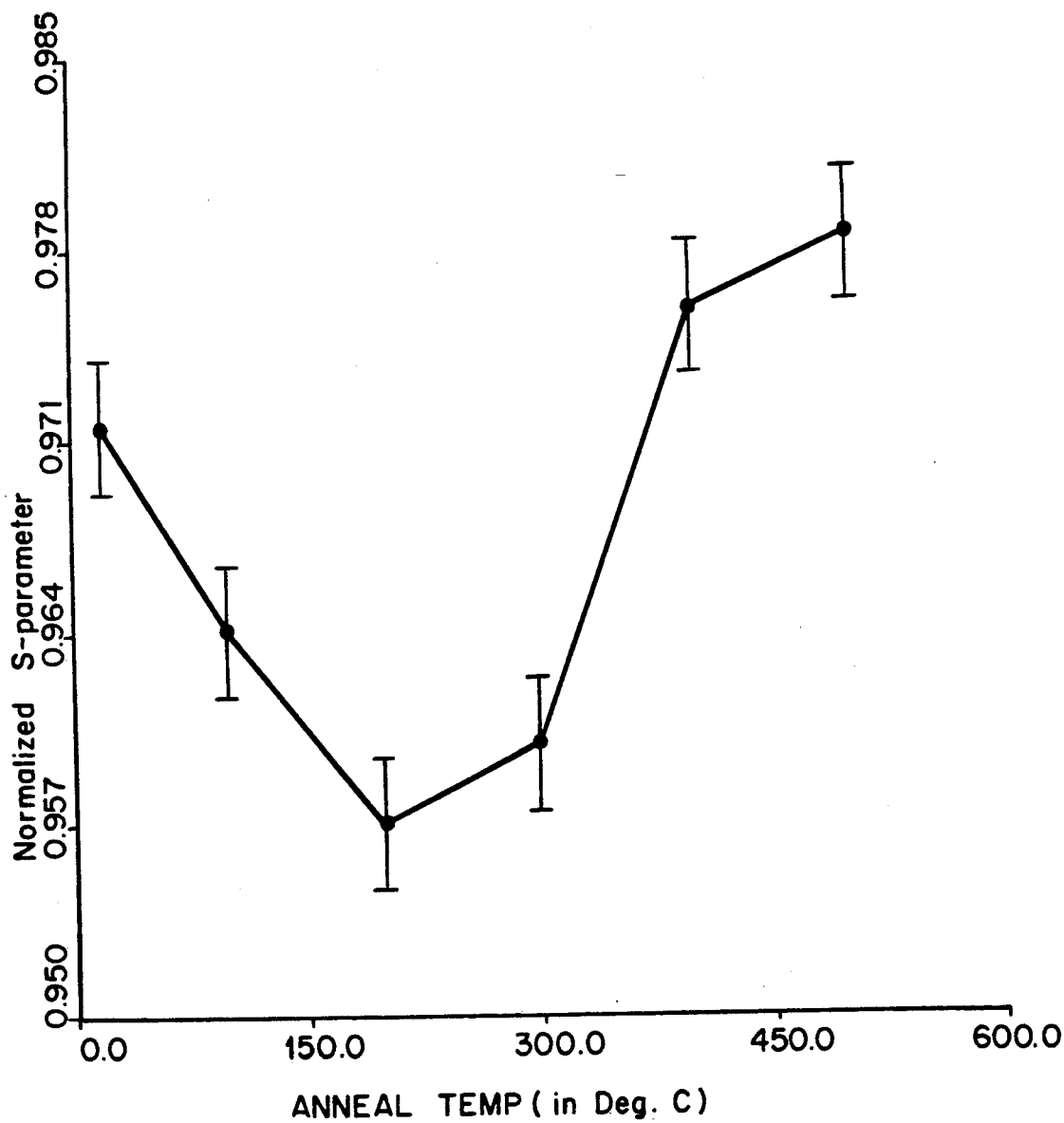
Figure 3C:
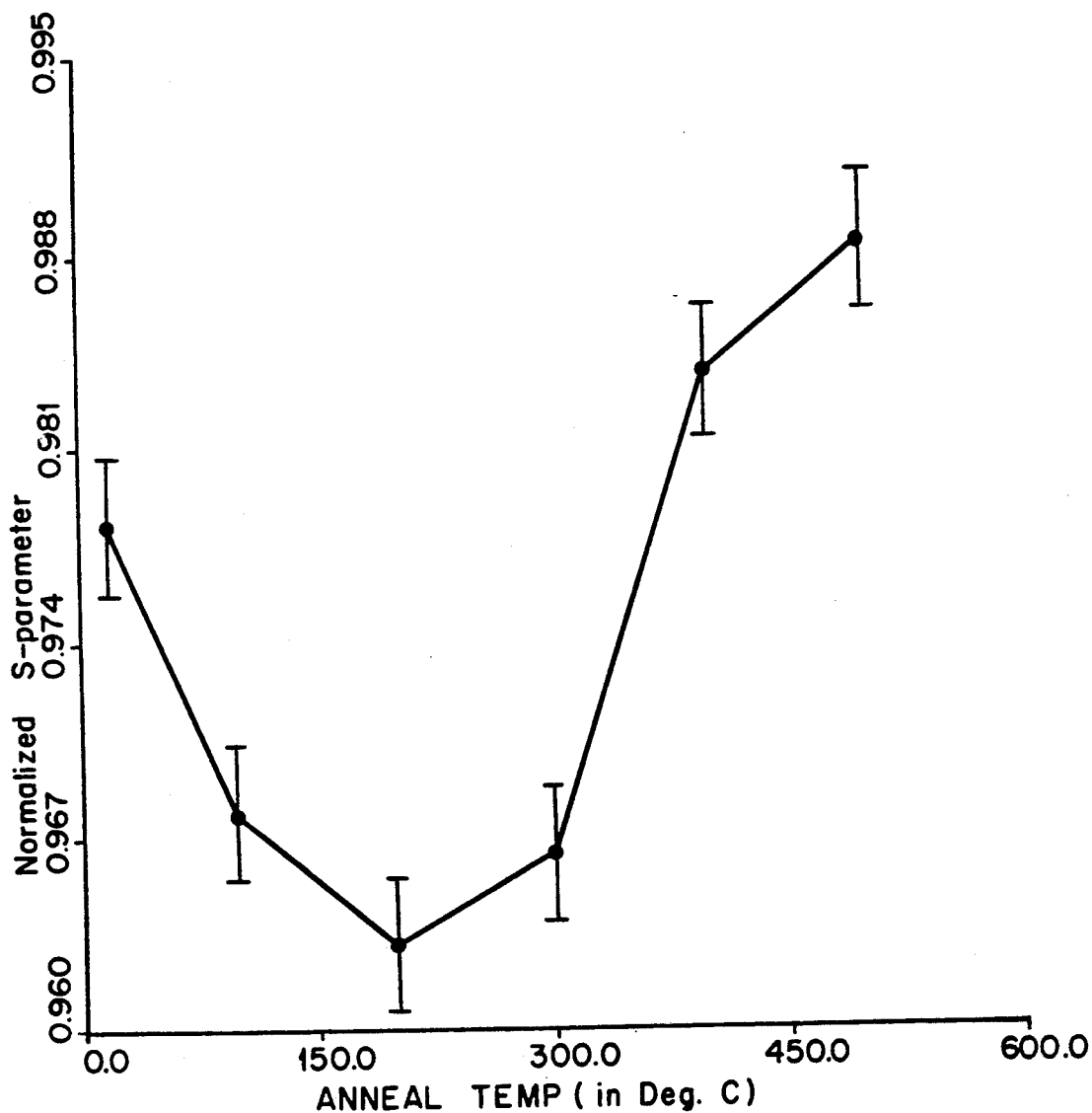

FIGS. 3A, 3B and 3C graphically show the normalized S-parameter values as a function of annealing temperature for different incident positron energies of 3.47 keV, 4.47 keV and 5.47 keV, respectively. In each of these experiments the annealing temperatures were increased from room temperature in five (5) increments of 100° C. Normalization is achieved by dividing the observed S-parameter for a given incident positron energy by the corresponding S-parameter value for the bulk sample. Bulk S-parameter corresponds to the S-parameter recorded for higher incident positron energies, in this Example 10.0–20 keV.

A dramatic lowering of the normalized S-parameter was observed at annealing temperatures in the range of 200°–400° C., for beam energies corresponding to the interface region. This lowering effect was observed for both the room temperature and elevated temperature measurements. We have concluded that this change is triggered by a decrease in the density of interface states or by a decrease in the number of positron traps at the interface. A positron annihilating from a trapped state has a higher probability of encountering a slow moving electron. As a result the annihilation spectra from a trapped site will produce a much sharper spectrum as opposed to other electrons, which will result in a higher S-parameter.

EXAMPLE 2

This Example was carried out in the same manner as Example 1, except that the beam energy was varied from 0.05 to 20.0 keV in steps of 0.25 keV. As in Example 1, for each energy value the S-parameter was evaluated with 1 million events recorded in the annihilation photopeak. The sample 25 was annealed in steps of 10020 C. and the detected S-parameter data versus energy was recorded for each of the elevated temperatures. After each thermal cycle, the sample was slowly cooled down to room temperature and the S-parameter was recorded. The length of time from annealing through data acquisition at each temperature was ~6 hours.

As the positron energy was increased from 0.05 to 20.0 keV, the positron beam started to penetrate deeper into the sample. The mean penetration depth has power-law dependence on incident positron energy see, Schultz and Lynn (1988) supra., and is therefore used as an alternate variable for incident energy. Hence, the measured S-parameter corresponds to the $SiO_2$ surface, $SiO_2$ overlayer, oxide-silicon interface, and bulk silicon, respectively.

FIG. 4 shows the normalized S-parameter data as a function of the mean implantation depth (i.e. incident positron energy) for measurements performed at room temperature before (●) and after (○) annealing at 200° C. The tick mark at 1081 Å on theorizonal axis indicates the interface location. The first data points on the left for each set are associated with the surface parameter, $S_s$. The initial rise corresponds to the overlayer $S_o$ and the immediate lowering to the interface $S_i$. The curve saturates at a bulk value $S_b$ for large implantation depth, i.e. large implantation energy.

FIGS. 5A and 5B show the normalized S-parameter curves as a function of annealing temperature for four mean implantation depths, 240 Å(●), 1130 Å(o), 2775 Å(■), and 4785 Å(□). The measurements were performed at the temperature for, FIG. 5A, and at room temperature after each annealing cycle for FIG. 5B. The 1130 Å curves probe the interface region and show a reduction for temperatures between 200°–400° C. The lines through the data points are drawn as a guide to the eye.

DISCUSSION AND ANALYSIS

In conventional capacitance-voltage (CV) measurements, such as the type employed to study metal-oxide-semiconductor (MOS) structures, an ac bias is applied across the system and capacitance vs voltage response of the system is recorded at various frequencies (1 Hz to 1 MHz). The data is used to deduce various interface related parameters. The positron annihilation technique can be developed to produce an analogous result. Moreover, the method of the present invention may provide more precise information about interface states and in less time, than can be obtained by using the conventional CV measurement technologies. When an ac bias is applied to the sample, the thermalized positrons will respond to the applied bias in a way similar to the majority and minority carriers in the semiconductor. Most of the interface properties studied using the CV-technique are the result of the charge carrier distributions around the interface. Some of these charge carriers get trapped at defect sites with characteristic time constants. The resulting trap centers will be charged. Then, when an ac bias is applied, since the amplitude of the bias is continuously changing in accordance with the applied frequency and since the capture and emission of carriers from trap centers are not infinitely fast, the trap centers will be populated differently depending on the applied ac frequency. This changing behavior is used in standard CV-measurement to extract various parameters relevant to the interface. The positron annihilation spectra originating around a trap site will be sensitive to this changing behavior of the trap centers as the applied frequency is varied. Thus the positron annihilation spectra can be used to monitor the capture and decay characteristics of these trap centers.

Annealing studies on thermally grown $SiO_2$/Si sample using CV-measurements (capacitance-voltage measurement) has shown that the interface state densities can be reduced by annealing the sample. These CV annealing studies are in agreement with the conclusions reached based on the above Examples; see Nicollin et al. "MOS (Metal Oxide Semiconductor)", *Physics and Technology*, p. 789, John Wiley & Sons, New York, (1982). Specifically, there appears to be a striking similarity between the 1130 Å curves in FIGS. 5A and 5B to the corresponding low temperature annealing measurements performed with the CV-techniques described by Nicollin et al. at page 789, which has been reproduced as FIG. 6. Based on these similarities, the inventors herein identified a direct correlation between the reduction in normalized S-parameter to the decrease in the density of the interface states. As described in more detail below, by comparing to a known behavior of the interface state density, these Examples demonstrate that the positron annihilation studies on $SiO_2$/Si sample can be used to extract the density of interfacial states. Even though CV-measurements can provide information about the interface state densities, the CV-technique is destructive in nature, since it requires ohmic (metallic) contacts to be evaporated onto either face of the wafer to make electrical contacts. In addition since this process is time consuming, CV-measurements can be performed only on a limited number of wafers as a random, destructive on-line probe at the production stage. By contrast, the present invention can be implemented as an on-line, non-destructive probe for the rapid characterization of the interface properties to monitor the quality of the wafers.

It is interesting to note that the sensitivity of these measurements is not bound by the current limit set by the CV-measurement techniques. Since positrons are capable of seeking out trap sites, a well controlled experiment can probe density of states in a convenient way. The current lower limit on density of states measured by CV-techniques is on the order of $10^{10}$ $cm^{-2}eV^{-1}$. Even though present semiconductor device performances are satisfactory with this value of interface state densities, in future as the memory devices are decreased in size, a much lower value of interface state density will be preferred. Hence, in addition to being a quality control probe on the production line of silicon wafers, characterizing interface states with positron annihilation spectra will help to identify better fabrication procedures, unattainable with current techniques.

As pointed above, CV-techniques require metallic contacts on either side of the wafer. Since these metallic contacts (usually aluminium) start to interact with the wafer at high temperatures (>600), the CV-techniques become less reliable at high temperatures. On the other hand the positron annihilation method of the present invention does not pose this problem. The positron annihilation method can also be used to identify concentrations of chemical impurities present in solid heterostructures; for example see Asoka-Kumar, Lynn et al., *J. Appl. Phys.*, 69, 6603–6606 (May 1991) in which hydrogen was introduced at the interface.

The above Examples have been performed on a Si-$O_2$/Si wafer containing a 1081 Å-thick oxide layer. Since this oxide layer is thicker than the state-of-art oxide layers used in the semiconductor industry, it is worth pointing out that the sensitivity of the present invention increases with thinner oxide layer systems. The increase in sensitivity of the present invention with thermal oxide layer systems is due to the following reasons. When a positron beam of a given energy strikes a solid, all of the positrons are not stopped at exactly same distance from the surface of the solid. The stopping profile will be broadened by the large number of elastic and inelastic collisions of positrons before thermalization. Thus, the stopping profile of positrons will become wider as the beam energy is increased. In order to penetrate a thin oxide layer, a lower incident positron beam energy is required. Therefore, the stopping profile of positrons incident on a thin oxide layer will be narrower and will be confined near to the interface region when the beam energy is tuned for a mean penetration depth corresponding to the oxide/Si interface. Accordingly, with a thinner oxide layer the present invention becomes more sensitive due to the increased number of positrons confined to the interface and contributing to the interface signal, thus making it a promising new method of characterizing interfaces in heterostructures.

In performing these Examples, when the normalized S-parameter corresponding to the interface region is plotted (see FIGS. 3–5) as a function of the annealing temperature, a dramatic change is observed for temperature values in the range of 200°–400° C. Since these changes are seen both in the room temperature measurement (FIG. 5B), and in the elevated temperature measurements (FIG. 5A), at first the origin of the observed changes was not readily apparent. After an extensive analysis of the literature related to SiO$_2$/Si heterostructures, the inventors located two reports of investigations on low-temperature annealing performed by the standard CV-techniques on the SiO$_2$/Si heterostructures; see, Yeow et al. *J. Phys. D: Appl. Phys.*, 8, 1495 (1975) and Zhang et al., *Appl. Surf. Sci.*, 39, 374 (1989). Both of these reports showed that a 200°–400° C. annealing reduced the interface state density. The inventors, therefore, concluded that the strong similarity between the curves obtained in Example 1 (see FIGS. 3A, 3B and 3C) with the CV-measurement curve obtained by these investigators (compare with FIG. 6 reproduced from p. 374 of Zhang et al. (1989) supra. was because the signal obtained by the present invention is a direct function of the decrease in the interface density.

In these Examples, the thermalized positrons become localized to sites related to the interface states. A positron annihilating from a trapped site (which usually has more open volume for the positron to become localized, as discussed in *Positrons in Solids*, Hautojärvi (Ed.), Springer-Verlag, New York (1979)) has a higher probability of encountering a slow moving electron as opposed to freely diffusing positrons. As a result, the annihilation photons from a trapped state will produce a sharper pair momentum spectrum. A sharper photopeak will correspond to a higher S-value. Thus, when the density of the interface states are reduced, the number of positrons annihilating from the specific trapped sites are reduced, and this will in turn reduce the normalized S-parameter which was observed in these Examples.

The CV-measurement data has established that the interface state densities in the Si/SiO$_2$ heterostructure can be reduced by annealing at temperatures ranging from 200° to 400° C.; see, Nicollin et al. (1982), supra. The exact annealing temperature that is required to produce the lowest interface state density varies depending on the wafer processing method. If the sample is heated beyond 400° C., the CV-method shows an increase in the interface state density. An identical behavior for the normalized S-parameter curves corresponding to the interface region as shown in FIGS. 5A and 5B (see curves with mean depth of 1130 Å). However, the relative shift in temperatures corresponding to the location of the minimum of the curves in these two figures is not completely understood.

When most of the positrons are implanted beyond the interface, the changes in the normalized S-values decrease slowly indicating that a large fraction of the positrons diffuse back to the interface where they become trapped. For Example, from the theoretical modeling described below, ~40% of the positrons implanted at a mean depth of 1235 Å diffused back to the interface and ~10% diffused back to the interface when implanted at a mean depth of 4785 Å.

The normalized S-parameter curve (shown in FIG. 4) can be understood by calculating the probability of positron annihilation from different locations of the solid by solving a one dimensional, steady-state, diffusion-annihilation equation, reported previously by Schultz and Lynn (1988) supra, as follows:

$$\frac{\partial J(z)}{\partial z} + P(E,z) - A(z) = 0, \quad (1)$$

where $J(z)$ is the positron flux at a depth z, $A(z)$ is the corresponding annihilation rate, and E is the incident positron beam energy. The function $P(E,z)$ is the implantation profile of thermalized positrons that can be approximated by a Makhovian distribution; also see, Kumar & Lynn, "Implantation Profile of Low-energy Positrons in Solids", *Appl. Phys. Lett.* 57, 1634–1636 (15 Oct. 1990); the disclosure of which is incorporated by reference herein.

Solving equation (1) the fraction of positrons annihilating from a given depth can be obtained. The numerical method described by the inventors is used to solve the annihilation-diffusion equation by slicing the solid into thin slabs along planes perpendicular to the incident beam direction. The resulting annihilation fraction of positrons in each slab, $F_j$ can be used to fit the experimental S-parameter values $$S_{expt} = \sum_{j=1}^{\text{no. of slabs}} S_j F_j \quad (2)$$

For a multilayered system like the SiO$_2$/Si heterostructure tested in these Examples, the $S_j$-values of all the slabs belonging to a given layer will be assumed identical. Hence, from the fitting procedure the $S_j$ values corresponding to surface, overlayer, interface, and bulk silicon (denoted by $S_s$, $S_o$, $S_i$, and $S_b$, respectively) can be obtained. In the above fitting procedure, and consistent with the present data, we used an interface layer thickness of 10 Å. The fitted value of $S_b$ is used to calculate the normalized S-parameter values. The parameter $S_i$, when plotted as a function of annealing temperature (see FIGS. 3A–5B) show a reduction corresponding to annealing temperatures in the ranges of 200°–400° C., confirming the earlier assertion that the changes observed are associated with the interface region. Since a reduction in the S-parameter is observed both at elevated (FIG. 5A) and room temperature (FIG. 5B) measurements, it is highly unlikely that the observed reduction is associated with the changes in diffusion from electric field variations at the interface.

Further evidence for the above interpretation of change in interface trap density, as opposed to change in the nature of trapping site itself, is obtained by analyzing the observed annihilation spectra in the Ge detector. The different regions of the annihilation photopeak represent different momentum densities of the annihilating electrons. An R-parameter can be defined in the same manner described by Mantl and Triftshauser, *Phys. Rev. B*, 17, 1645 (1978); and in *Positrons in Solids*, Hautojarvi (ed.), Springer-Verlag, New York, (1979), by taking the ratio of changes in different regions of the annihilation spectra sensitive to the nature of the trap sites and not the density. The R-parameter has been found to be independent of the concentration of trap sites and trapping rates; see, Mantl and Triftshauser (1978) supra., and will be a constant when the nature of the trapping sites are not changing. The R-parameter for the interface region remained constant (within experimental uncertainties) throughout the temperature analyzed, supporting the conclusion that the interface density variation is the cause of the changes observed in the normalized S-parameter.

One way to explain the changes at the interface is based on the activation of trap sites by hydrogen. When Si/SiO₂ heterostructures are annealed around 300° C. it has been suggested by Fare et al., in *J. Appl Phys.*, 63, 5507 (1988) that hydrogen is liberated from the oxide layer and may be the reason for the small rise observed in the normalized S-parameter curve corresponding to 240 Å of FIGS. 5A and 5B. These hydrogen liberated from the oxide layer can neutralize the trap sites and therefore can change the S-parameter. Beyond 400° C., the captured hydrogen is again liberated from the interface which causes a subsequent increase in the positron trap site concentration. To test this scenario, the same sample used in the annealing series was exposed to hydrogen at various increasing temperatures. The results from this study support the proposed model and were presented by the inventor in "Proceedings of the 2nd Workshop on Researchers Using Positrons, Feb. 28— Mar. 1, 1991", *Japan Atomic Energy Research Institute, Takasaki Radiation Chemistry Research Establishment*, 9-2, 132-141 (1991), the disclosure of which is incorporated by reference herein.

The positron generated profiling of the interfacial properties of heterostructures will become more relevant for samples with thinner oxide layers, since the positron implantation profiles at the interface is spatially narrower. In order to test this assertion, the invention generated simulated data based on the theoretical model described earlier. This model data was then used to estimate the changes in the normalized S-parameter. All the parameters, except the interface S-parameter, $S_i$ are held fixed, the total S-parameter will vary in accordance with the changes in the $S_i$ value. The model data is generated to test the applicability of different oxide layer thickness, 100 Å and 1081 Å, respectively. As the oxide layer thickness was reduced, the changes observed in the normalized S-values became more pronounced. The simulated data and the size of the observed signal can also be used to estimate the sensitivity of the method of the present invention to changes in the interface density. By associating the observed S-parameter changes to typical changes observed in the interface densities of Si/SiO₂ heterostructures, as described by Niclllian et al. (1982) supra, and by extrapolating the S-parameter change to a 100 Å-thick oxide layer, the estimated values show that the technique may be sensitive to variations in the interface densities of $5 \times 10^9$ cm$^{-2}$eV$^{-1}$.

These Examples have shown for the first time that the positrons can be used to identify the variation of interface densities of the Si/SiO₂ heterostructures, which is of fundamental importance in studying the nature of specific interface states. By comparing a known behavior of the interface state density variation under low temperature annealing, the present invention provides an important positron annihilation technique for use as a rapid, non-destructive characterization tool to study, test and analyze interface properties in multilayer structures. The present invention can be combined with other techniques, such as CV measurements, positron life-time spectroscopy and 2D-ACAR (Two Dimensional Angular Correlation Annihilation Radiation) to provide detailed information of the interfacial structure along with the real momentum distribution of the electrons participating in the annihilation process; see, Schultz and Lynn (1988) supra. A real momentum distribution of the many electron system at the interface will improve the understanding of the interface behavior and will be useful in discriminating between various structural models proposed for the interface structure.

A compact, variable-energy positron beam of high intensity, produced as described herein, can provide rapid information about manufacturing flaws at the production stage of SiO₂/Si wafers by examining changes in the normalized S-parameter. It is postulated that a normalized S-parameter measurement can be very sensitive to changes in the interface state densities and can be used as a non-destructive probe to characterize the interface state density in semiconductor heterostructures. The normalized S-parameter measurement can also be used as a quality control probe for detecting defects in thin multilayered systems. Therefore, it is believed that the method and apparatus described by the present invention can be exploited to develop a very important quality control probe in the semiconductor industry.

Thus, while there have been described what are the presently contemplated preferred embodiments of the present invention, further changes and modifications could be made by those skilled in the art without departing from the scope of the invention, and it is contemplated to claim all such changes and modifications.

We claim:

1. A method for characterizing an interfacial electron state in a solid heterostructure using a positron beam to probe the solid heterostructure, which comprises:
   (a) directing a positron beam having a known energy level at a point of a solid heterostructure, wherein said energy level is sufficient for said positron beam to penetrate said solid heterostructure and contact electrons at trap sites at an interface of the solid heterostructure;
   (b) detecting the number and energy of gamma rays emitted from said solid heterostructure as a result of positrons from said positron beam annihilating with said electrons at the trap sites of the solid heterostructure;
   (c) quantifying the data obtained in step (b) as a function of Doppler broadening of a photopeak about 511 keV created by the annihilation of said positrons and said electrons at the trap sites at the interface of said solid heterostructure; and (d) comparing the function of the data quantified in step (c) with a known corresponding function of the Doppler broadening of the annihilation photopeak about 511 keV for a positron beam directed at the same material of known interface state density, whereby said comparison facilitates characterization of the interface sate density of the solid heterostructure at points corresponding to the penetration of positrons having said energy level into the interface of the solid heterostructure.

2. A method according to claim 1, wherein the known function compared in step (d) is obtained as a result of directing a positron beam at another point of said solid heterostructure of step (a).

3. A method according to claim 1, wherein said known function compared in step (d) is obtained by directing a second positron beam at the same point of a solid heterostructure as in step (a); and wherein a physical or chemical condition in the manufacturer or treatment of said solid heterostructure is varied prior to directing said second positron beam at the solid heterostructure.

4. A method according to claim 3, wherein said variation in physical condition is the annealing temperature at the interface of the solid heterostructure.

5. A method according to claim 3, wherein said variation in chemical condition is the presence of an impurity at the interface of the solid heterostructure.

6. A method as recited in claim 1, wherein said function is an S-parameter.

7. A method as recited in claim 1, wherein said function is a W-parameter.

8. A method as recited in claim 1, wherein said function is a normalized S-parameter.

9. A method according to claim 1, wherein said solid heterostructure is a $SiO_2/Si$ MOS.

10. A method according to claim 1, wherein said known energy level is sufficient for said positron beam to penetrate said solid heterostructure and contact electrons at trap sites in a non-interface portion of the solid heterostructure.

11. A method according to claim 10, wherein said non-interface portion is in a bulk silicon portion of said solid heterostructure.

12. A method according to claim 10, wherein said non-interface portion is in an oxide layer of said solid heterostructure.

* * * * *